United States Patent [19]

Michael

[11] Patent Number: 5,112,688
[45] Date of Patent: May 12, 1992

[54] MICROCAPSULES CONTAINING HYDROPHOBIC LIQUID CORE

[75] Inventor: Daniel W. Michael, Cincinnati, Ohio

[73] Assignee: The Procter & Gamble Company, Cincinnati, Ohio

[21] Appl. No.: 624,484

[22] Filed: Dec. 6, 1990

Related U.S. Application Data

[63] Continuation of Ser. No. 316,252, Feb. 27, 1989, abandoned.

[51] Int. Cl.⁵ .............. B01J 13/06; C11D 17/00; A61K 7/46
[52] U.S. Cl. .................. 428/402.2; 264/41; 512/2; 512/4; 424/492; 252/8.6; 252/90; 252/174.11
[58] Field of Search .......... 428/402.2; 264/4.1, 264/4.3; 512/2, 4; 424/492; 252/8.6, 90, 174.11

[56] References Cited

U.S. PATENT DOCUMENTS

| | | | |
|---|---|---|---|
| 2,800,457 | 7/1957 | Green et al. | 428/402.2 |
| 2,800,458 | 7/1957 | Green | 428/402.2 |
| 3,041,289 | 6/1962 | Katchen et al. | 428/402.2 X |
| 3,104,980 | 9/1963 | Maierson | 428/402.2 |
| 3,201,353 | 8/1965 | Corben | 428/402.2 |
| 3,244,640 | 4/1966 | Studt et al. | 428/402.22 |
| 3,317,433 | 5/1967 | Eichel | 428/402.21 |
| 3,520,971 | 7/1970 | Benford | 428/402.2 |
| 3,533,958 | 10/1970 | Yurkowitz | 428/402.2 X |
| 3,676,363 | 7/1972 | Mosier | 424/492 X |
| 3,697,437 | 10/1972 | Fogle et al. | 428/402.2 X |
| 3,888,689 | 6/1975 | Maekawa et al. | 106/24 |
| 3,985,840 | 10/1976 | Hofacker | 428/402.2 |
| 4,010,038 | 3/1977 | Iwasaki et al. | 106/22 |
| 4,115,315 | 9/1978 | Marinelli | 428/402.2 |
| 4,145,184 | 3/1979 | Brain et al. | 8/137 |
| 4,234,627 | 11/1980 | Schilling | 252/174.11 |
| 4,394,287 | 7/1983 | Scarpelli | 424/492 X |
| 4,446,032 | 5/1984 | Munteanu et al. | 252/8.6 |

FOREIGN PATENT DOCUMENTS 1483542 8/1977 United Kingdom .

*Primary Examiner*—Robert L. Stoll
*Assistant Examiner*—John M. Covert
*Attorney, Agent, or Firm*—Robert B. Aylor; Richard C. Witte

[57] ABSTRACT

Microcapsules which are prepared using coacervation processes and/or which have a complex structure in which there is a large central core of encapsulated material, preferably perfume, and the walls contain small wall inclusion particles of either the core material or some other material that can be activated to disrupt the wall are disclosed. The microcapsules that are prepared by coacervation and contain perfume are especially desirable for inclusion in fabric softener compositions that have a pH of about 7 or less and which contain cationic fabric softener. The encapsulated perfume preferably does not contain large amounts of relatively water-soluble ingredients. Such ingredients are added separately to the fabric softener compositions. Ingredients that have high and low volatilities as compared to, e.g., the desired perfume, can either be added to, or removed from, the perfume to achieve the desired volatility.

11 Claims, No Drawings

MICROCAPSULES CONTAINING HYDROPHOBIC LIQUID CORE

This is a continuation of application Ser. No. 07/316,252 filed on Feb. 27, 1989 now abandoned.

BACKGROUND OF THE INVENTION

1. Field of the Invention

The present invention relates generically to microcapsules containing a hydrophobic liquid core. It also relates to the selection of specific materials for the cores and the capsules and preparation and uses of the microcapsules.

2. Background Art

Microencapsulation of various hydrophobic liquids is well known. Microcapsules have been suggested for encapsulation of perfumes, medicines, adhesives, dyestuffs, inks, etc. It has specifically been suggested to microencapsulate fragrances for use in liquid or solid fabric softeners. See, e.g., U.S. Pat. No. 4,446,032, Munteanu et al., issued May 1, 1984, incorporated herein by reference. The individual perfume and/or flavor compounds which can be encapsulated are also well known, having been disclosed in, e.g., U.S. Pat. No. 3,971,852, Brenner et al., issued Jul. 27, 1976; U.S. Pat. No. 4,515,705, Moeddel, issued May 7, 1985; U.S. Pat. No. 4,741,856, Taylor et al., issued May 3, 1988, etc., all of the above patents being incorporated herein by reference.

Microencapsulation techniques, including so-called "coacervation" techniques, are also well known, having been described, for example, in U.S. Pat. No. 2,800,458, Green, issued Jul. 23, 1957; U.S. Pat. No. 3,159,585, Evans et al., issued Dec. 1, 1964; U.S. Pat. No. 3,533,958, Yurkowitz, issued Oct. 13, 1970; U.S. Pat. No. 3,697,437, Fogle et al., issued Oct. 10, 1972; U.S. Pat. No. 3,888,689, Maekawa et al., issued Jun. 10, 1975; Brit. Pat. 1,483,542, published Aug. 24, 1977; U.S. Pat. No. 3,996,156, Matsukawa et al., issued Dec. 7, 1976; U.S. Pat. No. 3,965,033, Matsukawa et al., issued Jun. 22, 1976; and U.S. Pat. No. 4,010,038, Iwasaki et al., issued Mar. 1, 1977, etc., all of said patents being incorporated herein by reference.

Other techniques and materials for forming microcapsules are disclosed in U.S. Pat. No. 4,016,098, Saeki et al., issued Apr. 5, 1977; U.S. Pat. No. 4,269,729, Maruyama et al., issued May 26, 1981; U.S. Pat. No. 4,303,548, Shimazaki et al., issued Dec. 1, 1981; U.S. Pat. No. 4,460,722, Igarashi et al., issued Jul. 17, 1984; and U.S. Pat. No. 4,610,927, Igarashi et al., issued Sep. 9, 1986, all of said patents being incorporated herein by reference.

For certain utilities such as that disclosed in U.S. Pat. No. 4,446,032 it is desirable to have a strong capsule wall to permit preparation of finished compositions that contain microcapsules utilizing processes that tend to destroy capsule walls and yet have the capsules readily activated in some way during use.

SUMMARY OF THE INVENTION

This invention relates to microcapsules containing hydrophobic liquid cores. Such microcapsules comprise a relatively large central core of hydrophobic liquid material, e.g., cores having diameters in excess of about 50 microns. Preferably, the microcapsules have complex structures in which the capsule walls surrounding the central cores comprise substantial amounts of relatively small wall inclusion particles of core material and/or other materials, such as materials which can be activated by heat to disrupt the wall, said small wall inclusion particles having particle sizes of less than about 15 microns, preferably less than about 10 microns.

Microcapsules made by coacervation processes from gelatin and a polyanionic material, and especially such microcapsules having a complex structure, are particularly desirable for use in aqueous fabric softener compositions that comprise a cationic fabric softener and have a pH of about 7 or less.

Microcapsules having this complex wall structure can be conveniently made by coacervation processes in which at least a major portion of the material to be encapsulated is converted to an emulsion having particle diameters of more than about 50 microns and another smaller portion of the same material, or a different material, or mixtures thereof, is converted to an emulsion or suspension having particle diameters of less than about 15 microns before encapsulation, e.g., the coacervation process uses an emulsion with a bimodal distribution.

During a typical coacervation process for forming microcapsules, smaller hydrophobic emulsion wall inclusion particles will be encapsulated first and they in turn will coalesce around the larger emulsion core particles to form walls. All, or a portion of the small wall inclusion particles can be a different material than the central core material, preferably a material that can be activated by heat to disrupt the walls.

A visualization of the particles of this invention can be derived from U.S. Pat. No. 3,888,689, supra, FIGS. 1 and 2. FIG. 1 is representative of the particle structure, which has a large central core and a relatively thin wall. That thin wall, however, has a structure like the particle of FIG. 2 with small droplets/particles incorporated in the wall.

DETAILS OF THE INVENTION

This invention relates to improvements for microcapsules, especially for use in aqueous fabric softener compositions containing cationic fabric softeners and having a pH of about 7 or less. Preferably, the microcapsules contain perfume. The preferred wall materials are those typically used to form microcapsules by coacervation techniques. The materials are described in detail in the following patents incorporated herein by reference, e.g., U.S. Pat. Nos. 2,800,458; 3,159,585; 3,533,958; 3,697,437; 3,888,689; 3,996,156; 3,965,033; 4,010,038; and 4,016,098. The preferred encapsulating material is gelatin coacervated with a polyanion such as gum arabic and more preferably cross-linked with a cross-linking material such as glutaraldehyde.

The microcapsule walls herein preferably contain smaller wall inclusion "particles" (includes liquid droplets) having diameters that are no more than about 25%, preferably less than about 15%, more preferably less than about 10%, of the diameter of the central core portion of the microcapsule described hereinafter. Even more preferably, these inclusion particles have diameters that are from about 0.1% to about 10% of the central core's diameter.

The preferred smaller wall inclusion "particles" in the walls of the preferred microcapsules are preferably materials which can be activated, e.g., by heat, water, etc. They can be either solids or liquids. For example, volatile materials under conditions of increased temperature, or lowered pressure, will tend to break down the relatively small barriers between the small wall inclusion particles thereby creating a porous network in the wall surrounding the major amount of the desired encapsulated material. Similarly, if the wall is somewhat porous and the small wall inclusion particles are water-soluble, the water-soluble wall particles can be dissolved and removed during the wash and/or rinse steps of a laundry process to create a porous wall structure that will permit the hydrophobic core material to escape, e.g., during a fabric drying stage or during subsequent use after the relatively intact large microcapsules are entrapped in fabric. Such particles containing water-soluble wall inclusion particles would be used in dry or nonaqueous compositions.

The central core portions of the microcapsules are relatively large. The core portion should be at least about 50 microns in diameter, preferably from about 50 to about 350 microns, more preferably from about 75 to about 300 microns, and even more preferably from about 100 to about 250 microns in diameter. As pointed out in U.S. Pat. No. 3,888,689, supra, such microcapsules are very efficient since a relatively large amount of core material is surrounded by a relatively small amount of wall material. At least about 50%, preferably at least about 60%, and more preferably at least about 75% of the microcapsules are within the stated ranges.

The thinnest part of the wall around the central core in any microcapsule can vary from about 0.5 to about 50 microns, preferably from about 5 to about 25 microns. In complex microcapsules, the thinnest part of the wall is preferably at least about 2 microns.

The Core Material

As disclosed hereinbefore, especially in the patents that are incorporated by reference, many hydrophobic liquids can be encapsulated. Perfumes are especially desirable, and especially the perfume ingredients disclosed in U.S. Pat. No. 4,515,705, supra, and 4,741,856, supra. Encapsulated perfumes are extremely desirable for use in the aqueous fabric softener compositions of this invention. Encapsulated perfumes are more likely to survive the rinse process and the drying process and therefore are able to perfume the cleaned and dried clothes.

It is a specific and unique advantage of encapsulated materials such as perfumes that more volatile components can be delivered to, and retained on, fabrics during drying. Such volatile materials, such as, e.g., perfume ingredients, can be defined in a preferred way as having a vapor pressure greater than about 3 microns of mercury at 25° C. up to and including materials having vapor pressures of about 5,000 microns of mercury. Components having vapor pressures that are less than about 3 microns of mercury at 25° C. can also be delivered more effectively by microencapsulation, as set forth herein, than by simple incorporation. Such materials can include materials such as perfume ingredients classified as middle and top notes, which are sometimes desirable since many such notes can be used to convey an improved freshness impression.

Perfumes that are substantive to fabrics are especially desirable. Substantive perfumes are those that contain a sufficient amount of substantive perfume ingredients so that when the perfume is used at normal levels in a product such as an aqueous softener composition, it deposits and provides a noticeable benefit to people having normal olfactory acuity. These perfume ingredients typically have vapor pressures lower than those of the average perfume ingredient. They typically have molecular weights of 200 or more and are detectable at levels below those of the average perfume ingredient. Relatively substantive perfumes contain sufficient substantive perfume ingredients to provide the desired effect, typically at least about 1% and preferably at least about 10%. Such perfumes are attached to fabrics after they escape from the microcapsules and extend the effect.

In a preferred aspect of the invention, only a portion of the perfume is encapsulated. This is especially true for microcapsules that have walls prepared from coacervate materials. Complete perfume formulations typically contain perfume ingredients, as described hereinafter, that can interfere with the postulated release mechanism in aqueous fabric softener compositions, thus leading to inconsistent performance. It is highly desirable to add such ingredients to the aqueous fabric softener compositions without encapsulation.

In general, there are two types of perfume ingredients that are sometimes desirably excluded from perfume compositions that are encapsulated, especially coacervate microcapsules, and more especially from coacervate microcapsules that have a complex structure. Ingredients of the first type are those with excessive water solubility at temperatures that are reached, either during encapsulation or in subsequent product storage, such as phenyl ethyl alcohol, benzyl acetate, and certain low molecular weight terpene alcohols. It is desired that there be a slightly more hydrophobic character to the perfume than is typical. Small amounts of surface active ingredients are acceptable and can even be desirable for ease of emulsification and/or encapsulation. However, using a slightly more hydrophobic perfume appears to provide more consistently effective microcapsules, especially those with a complex structure, and those that are to be used in aqueous liquid fabric softener compositions.

Also, it may, or may not, be desirable to encapsulate very high boiling materials, e.g., those having boiling points in excess of about 300° C., in microcapsules containing perfume that are used in fabric softener compositions. Such materials lower the volatility of the total perfume so that they provide a benefit if the perfume composition is too volatile. However, if the perfume's volatility is already too low, they reduce the ability of the perfume to escape through the walls of the microcapsule during the drying step when such escape is desirable for the purpose of disrupting the walls and facilitating more complete release of the core material.

Perfume ingredients such as those described above can be encapsulated and will show deposition benefits. However, maximum benefit is usually obtained when water-soluble and excessively nonvolatile ingredients are excluded from the encapsulated perfume used in aqueous liquid fabric softener compositions.

Flavors including those disclosed in U.S. Pat. No. 3,971,852, supra, are also desirable core materials in the microcapsules that contain particles in the walls. Similarly, pharmaceutical materials and agricultural chemicals can be encapsulated in such particles. The combination structure of the preferred microcapsules disclosed herein provides a desirable combination of wall strength during processing and the ability to reduce wall strength (activate) in use by a variety of means including heating or exposure to moisture to remove the materials that are included in the wall. Such microcapsules, especially those formed by coacervation, are very useful in detergent compositions for improved release of the contents.

The Wall Material

The materials used to form the wall are typically, and preferably, those used to form microcapsules by coacervation techniques. The materials are described in detail in the patents incorporated hereinbefore by reference, e.g., U.S. Pat. Nos. 2,800,458; 3,159,585; 3,533,958; 3,697,437; 3,888,689; 3,996,156; 3,965,033; 4,010,038; and 4,016,098.

The preferred encapsulating material for perfumes that are to be incorporated into an aqueous low pH fabric softener composition containing cationic fabric softener is gelatin coacervated with a polyanion such as gum arabic and, preferably, cross-linked with glutaraldehyde. The preferred gelatin is Type A (acid precursor), preferably having a bloom strength of 300 or, less preferably, 275, then by increments of 25, down to the least preferred 150. A spray dried grade of gum arabic is preferred for purity. Although gelatin is always preferred, other polyanionic materials can be used in place of the gum arabic. Polyphosphates, alginates (preferably hydrolyzed), carrageenan, carboxymethylcellulose, polyacrylates, silicates, pectin, Type B gelatin (at a pH where it is anionic), and mixtures thereof, can be used to replace the gum arabic, either in whole or in part, as the polyanionic material.

Other preferred parameters, in addition to suitable agitation, include: (1) The use of from about 5 to about 25, preferably from about 6 to about 15, more preferably from about 7 to about 12, and even more preferably from about 8 to about 10, grams of gelatin per 100 grams of perfume (or other suitable material) that is encapsulated. (2) The use of from about 0.4 to about 2.2, preferably from about 0.6 to about 1.5, more preferably from about 0.8 to about 1.2, grams of gum arabic (or an amount of another suitable polyanion to provide an approximately equivalent charge) per gram of gelatin. (3) A coacervation pH of from about 2.5 to about 8, preferably from about 3.5 to about 6, more preferably from about 4.2 to about 5, and even more preferably from about 4.4 to about 4.8. (The pH range is adjusted to provide a reasonable balance between cationic charges on the gelatin and anionic charges on the polyanion.) (4) Effecting the coacervation reaction in an amount of deionized water that is typically from about 15 to about 35, preferably from about 20 to about 30, times the amount of the total amount of gelatin and polyanionic material used to form the capsule walls. Deionized water is highly desirable for consistency since the coacervation reaction is ionic is nature. (5) Using a coacervation temperature between about 30° C. and about 60° C., preferably between about 45° C. and about 55° C. (6) After the desired coacervation temperature is reached, using a cooling rate of from about 0.1° C. to about 5° C., preferably from about 0.25° C. to about 2° C. per minute. The cooling rate is adjusted to maximize the time when the coacervate gel walls are being formed. For example, polyphosphate anions form coacervates that gel at higher temperatures, so the cooling rate should be kept slow at first and then speeded up. Gum arabic forms coacervates that gel at lower temperatures, so the cooling rate should be fast at first and then slow.

The gelatin/polyanion (preferably gum arabic) wall is preferably cross-linked. The preferred cross-linking material is glutaraldehyde. Suitable parameters, in addition to suitable agitation, for cross-linking with glutaraldehyde are: (1) The use of from about 0.05 to about 2.0, preferably from about 0.5 to about 1, grams of glutaraldehyde per 10 grams of gelatin. (2) Cooling the microcapsule slurry to a temperature of less than about 10° C. and letting it remain there for at least about 30 minutes before adding the glutaraldehyde. The slurry is then allowed to rewarm to ambient temperature. (3) Keeping the pH below about 5.5 if the cross-linking reaction is over about 4 hours in length. (Higher pH's and/or temperatures can be used to shorten the reaction time.) (4) Excess glutaraldehyde is removed to avoid excessive cross-linking by washing with an excess of water, e.g., about 16 times the volume of the capsule slurry. Other cross-linking agents such as urea/formaldehyde resins, tannin materials such as tannic acid, and mixtures thereof can be used to replace the glutaraldehyde either in whole or in part.

The coacervate microcapsules of this invention are particularly effective in providing protection to perfume compositions in aqueous fabric softening compositions that contain a cationic fabric softener, and especially those compositions having a pH of about 7 or less, more preferably from about 3 to about 6.5. The most preferred capsules have the complex structure in which the microcapsule walls contain small droplets of the perfume. Although not wishing to be bound by theory, it is believed that the wall formed by the gelatin/gum arabic coacervate interacts with the softener matrix. This interaction probably involves an exchange of ionic species and interaction with electrolyte and/or surfactants in the formula. These interactions result in a swelling of the wall that softens it somewhat while maintaining the barrier properties that protect the perfume. The swollen particle is more easily trapped in the fabric during the rinse cycle. Also, in the rinse cycle, the large change from the highly acidic aqueous fabric softener composition that has high concentrations of electrolyte and surfactant to the relatively dilute conditions of the rinse liquor further softens the wall.

The swollen, softened microcapsules are then exposed, typically, to the heat and drying conditions of an automatic clothes dryer. As the perfume expands when it is heated and the wall of the microcapsule is dehydrated and cracks, the perfume escapes from the microcapsule while it is still in contact with the fabrics. Also, the perfume does not escape all at once, but rather over a period of time that typically extends past the time in the dryer. This "controlled" release minimizes the loss of perfume during the drying step when the perfume can escape out the exhaust of the automatic clothes dryer. This combination of ion exchange, swelling, and dehydration/cracking provides a totally unexpected new mechanism for the release of the perfume from the coacervate microcapsules that is entirely different from the mechanism associated with other microcapsules such as those prepared from urea and formaldehyde. With those other capsules a shearing or crushing action is required to destroy the capsule wall and provide release of the perfume. The gelatin coacervate capsules are not as strong as e.g., urea/formaldehyde capsules, but have been found to provide sufficient protection while at the same time providing superior release of the perfume. The gelatin coacervate microcapsules are also superior to capsules made from water-soluble materials, since the walls of such capsules dissolve in aqueous products and release the perfume material prematurely.

In addition to the coacervation encapsulates, other microencapsulation processes can be used including those described in U.S. Pat. No. 4,269,724, supra; U.S. Pat. No. 4,303,548, supra; and U.S. Pat. No. 4,460,722, supra, all of said patents being incorporated herein by reference, to prepare the preferred complex structure where the wall contains small "particles" that can weaken the wall and thus promote release.

The complex wall structures will typically contain from about 1% to about 25%, preferably from about 3% to about 20%, more preferably from about 5% to about 15%, and even more preferably from about 7% to about 13%, of the weight of the core material of wall inclusion material having particle sizes as set forth hereinbefore. The particles included in the wall can be either the central core material, especially when the central core material is volatile, or can be different. When the central core material is not very volatile, additional more volatile materials can be added to the core material, and/or the particles in the walls, to increase the volatility (pressure), e.g., when heat is applied. Volatile solvents, compounds that break down upon the application of heat; compounds that dissolve when exposed to water; etc., can all be used. The goal is to have a very strong wall during processing and storage and then to decrease the strength of the wall at a desired time and thus allow the core material to escape, either all at once, or slowly, by passing through the resultant more porous wall structure. This complex wall structure is very important if the only mechanism for destroying the wall is mechanical action as in microcapsules formed from urea and formaldehyde. It is also very desirable for a coacervate microcapsule containing perfume in an aqueous fabric softener composition.

A preferred volatile material for addition to the core material, preferably in a minor amount, is a hydrocarbon such as dodecane, which increases the hydrophobic nature of the core material, has very little odor, and has a boiling point that is sufficiently high to avoid premature formation of pressure but low enough to be activated in a conventional automatic clothes dryer. Such volatile hydrocarbons include, especially, straight chain hydrocarbons containing from about 6 to about 16, preferably from about 10 to about 14, carbon atoms such as: octane; dodecane; and hexadecane. Both these highly volatile materials and the high boiling fractions of the perfume described hereinbefore can be used to adjust the volatility of the perfume, or other encapsulated material to the desired point, either up or down.

Other preferred materials that can be incorporated into the wall include short chain alkyl ($C_1$-$C_4$) esters of phthalic acid, d-limonene, mineral oil, silanes, silicones and mixtures thereof.

In order to obtain even distribution of microcapsules in aqueous fabric softener compositions, it is desirable to maintain the density of the microcapsules close to that of the fabric softener composition. Such fabric softener compositions typically have densities in the range of from about 0.95 to about 0.99 grams per cubic centimeter. Accordingly, the density of the microcapsule is desirably between about 0.85 and about 1.2, preferably between about 0.9 and about 1 grams per cubic centimeter. The aqueous fabric softener compositions typically have viscosities sufficiently high enough to stabilize the microcapsules against separation as long as the particle size of the microcapsules is less than about 350 microns and the weight per cent of the microcapsules in the composition is less than about 1.5%.

The Fabric Softeners

Fabric softeners that can be used herein are disclosed in U.S. Pat. Nos. 3,861,870, Edwards and Diehl; 4,308,151, Cambre; 3,886,075, Bernardino; 4,233,164, Davis; 4,401,578, Verbruggen; 3,974,076, Wiersema and Rieke; and 4,237,016, Rudkin, Clint, and Young, all of said patents being incorporated herein by reference.

A preferred fabric softener of the invention comprises the following:

Component I(a)

A preferred softening agent (active) of the present invention is the reaction products of higher fatty acids with a polyamine selected from the group consisting of hydroxyalkylalkylenediamines and dialkylenetriamines and mixtures thereof. These reaction products are mixtures of several compounds in view of the multifunctional structure of the polyamines (see, for example, the publication by H. W. Eckert in Fette-Seifen-Anstrichmittel, cited above).

The preferred Component I(a) is a nitrogenous compound selected from the group consisting of the reaction product mixtures or some selected components of the mixtures. More specifically, the preferred Component 1(a) is compounds selected from the group consisting of: (i) the reaction product of higher fatty acids with hydroxyalkylalkylenediamines in a molecular ratio of about 2:1, said reaction product containing a composition having a compound of the formula:

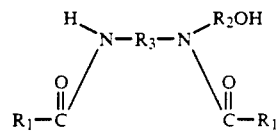

wherein $R_1$ is an acyclic aliphatic $C_{15}$-$C_{21}$ hydrocarbon group and $R_2$ and $R_3$ are divalent $C_1$-$C_3$ alkylene groups;

(ii) substituted imidazoline compounds having the formula:

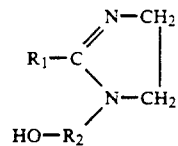

wherein $R_1$ and $R_2$ are defined as above; (iii) substituted imidazoline compounds having the formula:

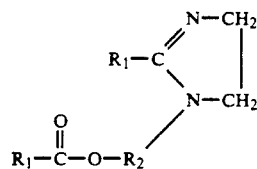

wherein $R_1$ and $R_2$ are defined as above;

(iv) the reaction product of higher fatty acids with dialkylenetriamines in a molecular ratio of about 2:1, said reaction product containing a composition having a compound of the formula:

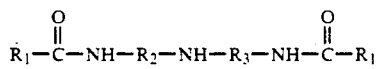

wherein $R_1$, $R_2$ and $R_3$ are defined as above; and (v) substituted imidazoline compounds having the formula:

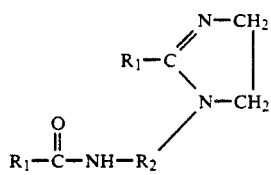

wherein $R_1$ and $R_2$ are defined as above; and mixtures thereof.

Component I(a)(i) is commercially available as Mazamide ® 6, sold by Mazer Chemicals, or Ceranine ® HC, sold by Sandoz Colors & Chemicals; here the higher fatty acids are hydrogenated tallow fatty acids and the hydroxyalkylalkylenediamine is N-2-hydroxyethylethylenediamine, and $R_1$ is an aliphatic $C_{15}$–$C_{17}$ hydrocarbon group, and $R_2$ and $R_3$ are divalent ethylene groups.

An example of Component I(a)(ii) is stearic hydroxyethyl imidazoline wherein $R_1$ is an aliphatic $C_{17}$ hydrocarbon group, $R_2$ is a divalent ethylene group; this chemical is sold under the trade names of Alkazine ® ST by Alkaril Chemicals, Inc., or Schercozoline ® S by Scher Chemicals, Inc.

An example of Component I(a)(iv) is N,N''-ditallowalkoyldiethylenetriamine where $R_1$ is an aliphatic $C_{15}$–$C_{17}$ hydrocarbon group and $R_2$ and $R_3$ are divalent ethylene groups.

An example of Component 1(a)(v) is 1-tallowamidoethyl-2-tallowimidazoline wherein $R_1$ is an aliphatic $C_{15}$–$C_{17}$ hydrocarbon group and $R_2$ is a divalent ethylene group.

The Component I(a)(v) can also be first dispersed in a Bronstedt acid dispersing aid having a pKa value of not greater than 6; provided that the pH of the final composition is not greater than 7. Some preferred dispersing aids are formic acid, phosphoric acid, and/or methylsulfonic acid.

Both N,N''-ditallowalkoyldiethylenetriamine and 1-tallowethylamido-2-tallowimidazoline are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, Journal of the American Oil Chemicals' Society, January 1978, pages 118–121). N,N''-ditallowalkoyldiethylenetriamine and 1-tallowamidoethyl-2-tallowimidazoline can be obtained from Sherex Chemical Company as experimental chemicals. Methyl-1-tallowamidoethyl-2-tallowimidazolinium methylsulfate is sold by Sherex Chemical Company under the trade name Varisoft ®475.

Component I(b)

the preferred Component I(b) is a cationic nitrogenous salt containing one long chain acyclic aliphatic $C_{15}$–$C_{22}$ hydrocarbon group selected from the group consisting of:

(i) acyclic quaternary ammonium salts having the formula:

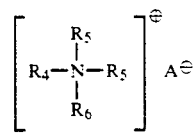

wherein $R_4$ is an acyclic aliphatic $C_{15}$–$C_{22}$ hydrocarbon group, $R_5$ and $R_6$ are $C_1$–$C_4$ saturated alkyl or hydroxyalkyl groups, and $A^\ominus$ is an anoin;

(ii) substituted imidazolinium salts having the formula:

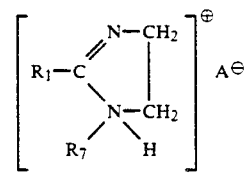

wherein $R_1$ is an acyclic aliphatic $C_{15}$–$C_{21}$ hydrocarbon group, $R_7$ is a hydrogen or a $C_1$–$C_4$ saturated alkyl or hydroxyalkyl group, and $A^\ominus$ is an anoin;

(iii) substituted imidazolinium salts having the formula:

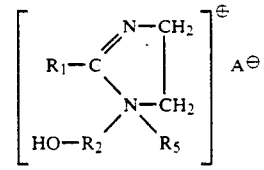

wherein $R_2$ is a divalent $C_1$–$C_3$ alkylene group and $R_1$, $R_5$ and $A^\ominus$ are as defined above;

(iv) alkylpyridinium salts having the formula:

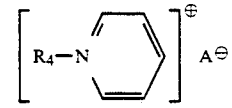

wherein $R_4$ is an acyclic aliphatic $C_{16}$–$C_{22}$ hydrocarbon group and $A^\ominus$ is an anoin; and (v) alkanamide alkylene pyridinium salts having the formula:

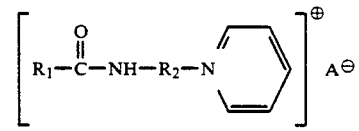

wherein $R_1$ is an acyclic aliphatic $C_{15}$–$C_{21}$ hydrocarbon group, $R_2$ is a divalent $C_1$–$C_3$ alkylene group, and $A^\ominus$ is an ion group;

and mixtures thereof.

Examples of Component I(b)(i) are the monoalkyltrimethylammonium salts such as monotallowtrimethylammonium chloride, mono(hydrogenated tallow) trimethylammonium chloride, palmityltrimethylammonium chloride and soyatrimethylammonium chloride, sold by Sherex Chemical Company under the trade names Adogen® 471, Adogen 441, Adogen 444, and Adogen 415, respectively. In these salts, $R_4$ is an acyclic aliphatic $C_{16}$-$C_{18}$ hydrocarbon group, and $R_5$ and $R_6$ are methyl groups. Mono(hydrogenated tallow)-trimethylammonium chloride and monotallowtrimethylammonium chloride are preferred. Other examples of Component I(b)(i) are behenyltrimethlammonium chloride wherein $R_4$ is a $C_{22}$ hydrocarbon group and sold under the trade name Kemamine® Q2803-C by Humko Chemical Division of Witco Chemical Corporation; soyadimethylethylammonium ethosulfate wherein $R_4$ is a $C_{16}$-$C_{18}$ hydrocarbon group, $R_5$ is a methyl group, $R_6$ is an ethyl group, and A is an ethylsulfate anion, sold under the trade name Jordaquat® 1033 by Jordan Chemical Company; and methyl-bis(2-hydroxyethyl)octadecylammonium chloride wherein $R_4$ is a $C_{18}$ hydrocarbon group, $R_5$ is a 2-hydroxyethyl group and $R_6$ is a methyl group and available under the trade name Ethoquad° 18/12 from Armak Company.

An example of Component I(b)(III) is 1-ethyl-1-(2-hydroxyethyl)-2-isoheptadecylimidazolinium ethylsulfate wherein $R_1$ is a $C_{17}$ hydrocarbon group, $R_2$ is an ethylene group, $R_5$ is an ethyl group, and A is an ethylsulfate anion. It is available from Mona Industries, Inc., under the trade name Monaquat® ISIES.

A preferred composition contains Component I(a) at a level of from about 50% to about 90% by weight of Component I and Component I(b) at a level of from about 10% to about 50% by weight of Component I.

Cationic Nitrogenous Salts I(c)

Preferred cationic nitrogenous salts having two or more long chain acyclic aliphatic $C_{15}$-$C_{22}$ hydrocarbon groups or one said group and an arylalkyl group which can be used either alone or as part of a mixture are selected from the group consisting of:

(i) acyclic quaternary ammonium salts having the formula:

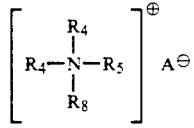

wherein $R_4$ is an acyclic aliphatic $C_{15}$-$C_{22}$ hydrocarbon group, $R_5$ is a $C_1$-$C_4$ saturated alkyl or hydroxyalkyl group, $R_8$ is selected from the group consisting of $R_4$ and $R_5$ groups, and $A^\theta$ is an anion defined as above;

(ii) diamido quaternary ammonium salts having the formula:

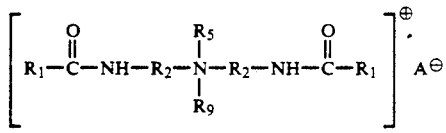

wherein $R_1$ is an acyclic aliphatic $C_{15}$-$C_{21}$ hydrocarbon group, $R_2$ is a divalent alkylene group having 1 to 3 carbon atoms, $R_5$ and $R_9$ are $C_1$-$C_4$ saturated alkyl or hydroxyalkyl groups, and $A^\theta$ is an anion;

(III) diamido alkoxylated quaternary ammonium salts having the formula:

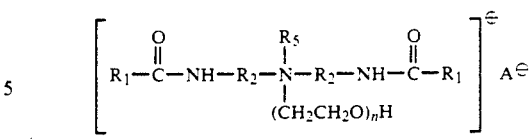

wherein n is equal to 1 to about 5, and $R_1$, $R_2$, $R_5$ and $A^\theta$ are as defined above;

(iv) quaternary ammonium compounds having the formula:

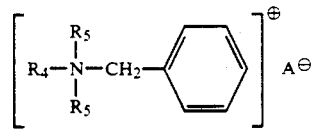

wherein $R_4$ is an acyclic aliphatic $C_{15}$-$C_{22}$ hydrocarbon group, $R_5$ i a $C_1$-$C_4$ saturated alkyl or hydroxyalkyl group, $A^\theta$ is an anion;

(v) substituted imidazolinium salts having the formula:

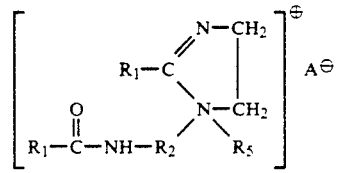

wherein $R_1$ is an acyclic aliphatic $C_{15}$-$C_{21}$ hydrocarbon group, $R_2$ is a divalent alkylene group having 1 to 3 carbon atoms, and $R_5$ and $A^\theta$ are as defined above; and (vi) substituted imidazolinium salts having the formula:

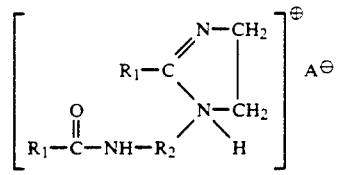

wherein $R_1$, $R_2$ and $A^\theta$ are as defined above; and mixtures thereof.

Examples of Component I(c)(i) are the well-known dialkyldimethylammonium salts such as ditallowdimethylammonium chloride, ditallowdimethylammonium methylsulfate, di(hydrogenated tallow)dimethylammonium chloride, distearyldimethylammonium chloride, dibehenyldimethylammonium chloride. Di(hydrogenated tallow)dimethylammonium chloride and ditallowdimethylammonium chloride are preferred. Examples of commercially available dialkyldimethylammonium salts usable in the present invention are di(hydrogenated tallow)dimethylammonium chloride (trade name Adogen 442), ditallowdimethylammonium chloride (trade name Adogen 470), distearyldimethylammonium chloride (trade name Arosurf® TA-100), all available from Sherex Chemical Company. Dibehenyldimethylammonium chloride wherein $R_4$ is an acyclic aliphatic $C_{22}$ hydrocarbon group is sold under the trade name Kemamine Q-2802C by Humko Chemical Division of Witco Chemical Corporation.

Examples of Component I(c)(ii) are methylbis(tallowamidoethyl)(2-hydroxyethyl)ammonium methylsulfate and methylbis(hydrogenated tallowamidoethyl)(2-hydroxyethyl)ammonium methylsulfate wherein $R_1$ is an acyclic aliphatic $C_{15}-C_{17}$ hydrocarbon group, $R_2$ is an ethylene group, $R_5$ is a methyl group, $R_9$ is a hydroxyalkyl group and A is a methylsulfate anion; these materials are available from Sherex Chemical Company under the trade names Varisoft 222 and Varisoft 110, respectively.

An example of Component I(c)(iv) is dimethylstearylbenzylammonium chloride wherein $R_4$ is an acyclic aliphatic $C_{18}$ hydrocarbon group, $R_5$ is a methyl group and A is a chloride anion, and is sold under the trade names Varisoft SDC by Sherex Chemical Company and Ammonyx® 490 by Onyx Chemical Company.

Examples of Component I(c)(v) are 1-methyl-1-tallowamidoethyl-2-tallowimidazolinium methylsulfate and 1-methyl-1-(hydrogenated tallowamidoethyl)-2-(hydrogenated tallow)imidazolinium methylsulfate wherein $R_1$ is an acyclic aliphatic $C_{15}-C_{17}$ hydrocarbon group, $R_2$ is an ethylene group, $R_5$ is a methyl group and A is a chloride anion; they are sold under the trade names Varisoft 475 and Varisoft 445, respectively, by Sherex Chemical Company.

A preferred composition contains Component I(c) at a level of from about 10% to about 80% by weight of said Component I. A more preferred composition also contains Component I(c) which is selected from the group consisting of: (i) di(hydrogenated tallow)dimethylammonium chloride and (v) methyl-1-tallowamidoethyl-2-tallowimidazolinium methylsulfate; and mixtures thereof. A preferred combination of ranges for Component I(a) is from about 10% to about 80% and for Component I(b) from about 8% to about 40% by weight of Component I.

Where Component I(c) is present, Component I is preferably present at from about 4% to about 27% by weight of the total composition. More specifically, this composition is more preferred wherein Component I(a) is the reaction product of about 2 moles of hydrogenated tallow fatty acids with about 1 mole of N-2-hydroxyethylethylenediamine and is present at a level of from about 10% to about 70% by weight of Component I; and wherein Component I(b) is mono(hydrogenated tallow)trimethylammonium chloride present at a level of from about 8% to about 20% by weight of Component I; and wherein Component I(c) is selected from the group consisting of di(hydrogenated tallow)dimethylammonium chloride, ditallowdimethylammonium chloride and methyl-1-tallowamidoethyl-2-tallowimidazolinium methylsulfate, and mixtures thereof; said Component 1(c) is present at a level of from about 20% to about 75% by weight of Component I; and wherein the weight ratio of said di(hydrogenated tallow)dimethylammonium chloride to said methyl-1-tallowamidoethyl-2-tallowimidazolinium methylsulfate is from about 2:1 to about 6:1.

The above individual components can also be used individually, especially those of I(c).

More biodegradable fabric softener compounds can be desirable. Biodegradability can be increased, e.g., by incorporating easily destroyed linkages into hydrophobic groups. Such linkages include ester linkages, amide linkages, and linkages containing unsaturation and/or hydroxy groups. Examples of such fabric softeners can be found in U.S. Pat. Nos. 3,408,361, Mannheimer, issued Oct. 29, 1968; 4,709,045, Kubo et al., issued Nov. 24, 1987; 4,233,451, Pracht et al., issued Nov. 11, 1980; 4,127,489, Pracht et al., issued Nov. 28, 1978; 3,689,424, Berg et al., issued Sep. 5, 1972; 4,128,485, Baumann et al., issued Dec. 5, 1978; 4,161,604, Elster et al., issued Jul. 17, 1979; 4,189,593, Wechsler et al., issued Feb. 19, 1980; and 4,339,391, Hoffman et al., issued Jul. 13, 1982, said patents being incorporated herein by reference.

Anion A

In the cationic nitrogenous salts herein, the anion $A^\ominus$ provides electrical neutrality. Most often, the anion used to provide electrical neutrality in these salts is a halide, such as fluoride, chloride, bromide, or iodide. However, other anions can be used, such as methylsulfate, ethylsulfate, hydroxide, acetate, formate, sulfate, carbonate, and the like. Chloride and methylsulfate are preferred herein as anion A.

Liquid Carrier

The liquid carrier is selected from the group consisting of water and mixtures of the water and short chain $C_1-C_4$ monohydric alcohols. The water which is used can be distilled, deionized, or tap water. Mixtures of water and up to about 15% of a short chain alcohol or polyol such as ethanol, propanol, isopropanol, butanol, ethylene glycol, propylene glycol, and mixtures thereof, are also useful as the carrier liquid.

Optional Ingredients

Adjuvants can be added to the compositions herein for their known purposes. Such adjuvants include, but are not limited to, viscosity control agents, emulsifiers, preservatives, antioxidants, bactericides, fungicides, brighteners, opacifiers, freezethaw control agents, shrinkage control agents, and agents to provide ease of ironing. These adjuvants, if used, are added at their usual levels, generally each of up to about 5% by weight of the composition.

Viscosity control agents can be organic or inorganic in nature. Examples of organic viscosity modifiers are fatty acids and esters, fatty alcohols, and water-miscible solvents such as short chain alcohols. Examples of inorganic viscosity control agents are water-soluble ionizable salts. A wide variety of ionizable salts can be used. Examples of suitable salts are the halides of the group IA and IIA metals of the Periodic Table of the Elements, e.g., calcium chloride, magnesium chloride, sodium chloride, potassium bromide, and lithium chloride. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desires of the formulator. Typical levels of salts used to control the composition viscosity are from about 20 to about 6,000 parts per million (ppm), preferably from about 20 to about 4,000 ppm by weight of the composition.

Examples of bactericides used in the compositions of this invention are glutaraldehyde, formaldehyde, 2-bromo-2-nitropropane-1,3-diol sold by Inolex Chemicals under the trade name Bronopol®, and a mixture of 5-chloro-2-methyl-4-isothiazolin-3-one and 2-methyl-4-isothiazoline-3-one sold by Rohm and Haas Company under the trade name Kathon® CG/ICP. Typical levels of bactericides used in the present compositions are from about 1 to about 1,000 ppm by weight of the composition.

Examples of antioxidants that can be added to the compositions of this invention are propyl gallate, available from Eastman Chemical Products, Inc., under the trade names Tenox ® PG and Tenox S-1, and butylated hydroxy toluene, available from UOP Process Division under the trade name Sustane ® BHT.

The present compositions may contain silicones to provide additional benefits such as ease of ironing and improved fabric feel. The preferred silicones are polydimethylsiloxanes of viscosity of from about 100 centistokes (cs) to about 100,000 cs, preferably from about 200 cs to about 60,000 cs. These silicones can be used as is, or can be conveniently added to the softener compositions in a preemulsified form which is obtainable directly from the suppliers. Examples of these preemulsified silicones are 60% emulsion of polydimethylsiloxane (350 cs) sold by Dow Corning Corporation under the trade name DOW CORNING ®1157 Fluid and 50% emulsion of polydimethylsiloxane (10,000 cs) sold by General Electric Company under the trade name General Electric ® SM 2140 Silicones. The optional silicone component can be used in an amount of from about % to about 6% by weight of the composition.

Soil release agents, usually polymers, are desirable additives at levels of from about 0.1% to about 5%. Suitable soil release agents are disclosed in U.S. Pat. Nos. 4,702,857, Gosselink, issued Oct. 27, 1987; 4,711,730, Gosselink and Diehl, issued Dec. 8, 1987; 4,713,194, Gosselink issued Dec. 15, 1987; and mixtures thereof, said patents being incorporated herein by reference. Other soil release polymers are disclosed in U.S. Pat. No. 4,749,596, Evans, Huntington, Stewart, Wolf, and Zimmerer, issued Jun. 7, 1988, said patent being incorporated herein by reference.

Other minor components include short chain alcohols such as ethanol and isopropanol which are present in the commercially available quaternary ammonium compounds used in the preparation of the present compositions. The short chain alcohols are normally present at from about 1% to about 10% by weight of the composition.

A preferred composition contains from about 0.1% to about 2% of perfume, at least a portion of which is encapsulated as set forth hereinbefore, from 0% to about 3% of polydimethylsiloxane, from 0% to about 0.4% of calcium chloride, from about 1 ppm to about 1,000 ppm of bactericide, from about 10 ppm to about 100 ppm of dye, and from 0% to about 10% of short chain alcohols, by weight of the total composition.

The pH (10% solution) of the compositions of this invention is generally adjusted to be in the range of from about 3 to about 7, preferably from about 3.0 to about 6.5, more preferably from about 3.0 to about 4. Adjustment of pH is normally carried out by including a small quantity of free acid in the formulation. Because no strong pH buffers are present, only small amounts of acid are required. Any acidic material can be used; its selection can be made by anyone skilled in the softener arts on the basis of cost, availability, safety, etc. Among the acids that can be used are hydrochloric, sulfuric, phosphoric, citric, maleic, and succinic acids. For the purposes of this invention, pH is measured by a glass electrode in a 10% solution in water of the softening composition in comparison with a standard calomel reference electrode.

The liquid fabric softening compositions of the present invention can be prepared by conventional methods. A convenient and satisfactory method is to prepare the softening active premix at about 72°–77° C., which is then added with stirring to the hot water seat. Temperature-sensitive optional components can be added after the fabric softening composition is cooled to a lower temperature.

The liquid fabric softening compositions of this invention are used by adding to the rinse cycle of conventional home laundry operations. Generally, rinse water has a temperature of from about 5° C. to about 60° C. The concentration of the fabric softener actives of this invention is generally from about 10 ppm to about 200 ppm, preferably from about 25 ppm to about 100 ppm, by weight of the aqueous rinsing bath.

In general, the present invention in its fabric softening method aspect comprises the steps of (1) washing fabrics in a conventional washing machine with a detergent composition; and (2) rinsing the fabrics in a bath which contains the above described amounts of the fabric softeners; and (3) drying the fabrics. When multiple rinses are used, the fabric softening composition is preferably added to the final rinse. Fabric drying can take place either in an automatic dryer (preferred) or in the open air.

All percentages, ratios, and parts herein are by weight unless otherwise indicated.

EXAMPLE

Making Complex Microcapsules

Complex microcapsules are prepared according to the following generic process. Details on the individual microcapsules are contained in Table 1.

The indicated amounts of gelatin with the indicated bloom strengths are dissolved into the indicated amounts of deionized water having the indicated temperatures in 800 ml beakers that serve as the main reaction vessels.

The indicated amounts of spray dried gum arabic are dissolved into the indicated amounts of deionized water having the indicated temperatures.

For microcapsules 1–5, the indicated amounts of a conventional perfume composition (containing about 30% orange terpenes (90% d-limonene), 10% linalyl acetate, 20% para tertiary butyl cyclohexyl acetate, 30% alpha ionone, and 10% para tertiary butyl alpha methyl hydrocinnamic aldehyde) which is fairly volatile, are emulsified with a laboratory mixer equipped with a Lightnin R-100 impeller into the gelatin solutions at high rpm (about 1600) such that after about 10 minutes the droplet size of the perfume is between about 1 and about 10 microns. This is the "fine emulsion."

The indicated amounts of the same perfume containing d-limonene are emulsified into the previously formed "fine emulsion" using the same mixer with a Lightnin A-310 impeller set at a lower rpm (about 350) such that after about 10 minutes a new, second, size distribution of perfume emulsion "particles" with a mean size of about 175 microns (coarse emulsion) are produced. The "fine emulsion" is still present. In microcapsules 6 and 7, the same process is used, but the perfume contains about 11.1% of ethyl amyl ketone; ionone alpha; ionone beta; ionone gamma methyl; ionone methyl; iso jasmone; iso menthone; and methyl beta-napthyl ketone and 11.2% of methyl cedrylone and the perfume is encapsulated with 30% dodecane.

The mixer is alowed to about 200 rpm.

The gum arabic solution is added and the indicated amounts of extra dilution deionized water at the indicated temperatures are added.

The pH is controlled as indicated. These pH's are selected by observing the pH at which the coacervates start forming. The solution/emulsions are cooled to room temperature in the indicated times. The solution/emulsions are then cooled to the indicated temperatures and allowed to stand for about 30 minutes. The coacervate is then cross-linked with the indicated amounts of a 25% solution of glutaraldehyde. The cross-linking reaction takes the indicated times during which slow increase to ambient temperature occurs.

TABLE 1

| Microcapsules | 1 | 2 | 3 | 4 |
|---|---|---|---|---|
| Gelatin (gms) | 15 | 8 | 12 | 10 |
| Bloom Strength | 225 | 275 | 275 | 250 |
| Water (gms) | 150 | 100 | 100 | 125 |
| Temperature (°C.) | 50 | 50 | 50 | 40 |
| Gum Arabic (gms) | 10 | 10 | 8 | 15 |
| Water (gms) | 250 | 250 | 200 | 250 |
| Temperature (°C.) | 40 | 45 | 45 | 40 |
| Total Perfume (gms) | 125 | 100 | 100 | 100 |
| Fine Emulsion (gms) | 25 | 10 | 15 | 15 |
| Coarse Emulsion (gms) | 100 | 90 | 85 | 85 |
| Dilution Water (gms) | 150 | 150 | 250 | 250 |
| Temperature (°C.) | 50 | 50 | 50 | 50 |
| Approx. pH range | 4.5–4.7 | 4.6–4.8 | 4.6–4.8 | 4.7–4.9 |
| Cooling time to room temperature (hours) | ~1 | ~1 | ~2 | ~2 |
| Initial cross-linking temperature (°C.) | 15 | 10 | 20 | 14 |
| Glutaraldehyde (gms of 25% solution) | 25 | 15 | 10 | 5 |
| Cross-linking time (hours) | 15 | 15 | 24 | 24 |

| Microcapsules | 5 | 6 | 7 |
|---|---|---|---|
| Gelatin (gms) | 10 | 15 | 8 |
| Bloom Strength | 300 | 200 | 300 |
| Water (gms) | 100 | 150 | 100 |
| Temperature (°C.) | 45 | 45 | 45 |
| Gum Arabic (gms) | 10 | 15 | 10 |
| Water (gms) | 250 | 300 | 225 |
| Temperature (°C.) | 45 | 45 | 45 |
| Total Perfume (gms) | 100 | 120 | 100 |
| Fine Emulsion (gms) | 10 | 20 | 5 |
| Coarse Emulsion (gms) | 90 | 100 | 95 |
| Dilution Water (gms) | 150 | 150 | 100 |
| Temperature (°C.) | 50 | 50 | 40 |
| Approx. pH range | 4.7–4.9 | 4.5–4.7 | 4.6–4.8 |
| Cooling time to room temperature (hours) | ~2 | ~2 | ~1 |
| Initial cross-linking temperature (°C.) | 5 | 10 | 5 |
| Glutaraldehyde (gms of 25% solution) | 4 | 1 | 15 |
| Cross-linking time (hours) | 16 | 24 | 4 |

Using the Complex Microcapsule

After analysis of the microcapsules for perfume content, a sufficient quantity of the microcapsules is added to fabric softener compositions having the formulas given hereinafter to provide the indicated amounts of perfume (The identify of the microcapsule which is used in each composition is indicated parenthetically after the amount of microcapsules.):

TABLE 2

| Ingredient | A Wt. % | B Wt. % | C Wt. % | D Wt. % |
|---|---|---|---|---|
| Adogen ® 448E-83HM[1] | 7.97 | 7.97 | 4.54 | 4.54 |
| Varisoft ® 445 Imidazoline[2] | 6.21 | 6.21 | 3.40 | 3.40 |
| Adogen ® 441[3] | 0.97 | 0.97 | 0.57 | 0.57 |
| Polydimethyl Siloxane (55%) | 0.61 | 0.61 | 0.32 | 0.32 |
| Silicone DC 1520 (20%) | 0.015 | 0.015 | 0.015 | 0.015 |
| Perfume (capsules) | 0.90(1) | 0.25(2) | 0.84(3) | 0.42(4) |
| Perfume (unencapsulated)[4] | 0.30 | 0.25 | — | 0.30 |
| Varonic ® T 220 D | 0.43 | 0.43 | 0.10 | 0.10 |
| Kathon ® | 0.034 | 0.034 | 0.034 | 0.034 |
| Tenox ® S-1 | 0.025 | 0.025 | — | — |
| Hydrochloric Acid (31.5%) | 1.25 | 1.25 | 0.62 | 0.62 |
| Calcium Chloride 25% Solution | 1.10 | 1.10 | 0.003 | 0.003 |
| Water | Balance | Balance | Balance | Balance |

| Ingredient | E Wt % | F Wt % | G Wt % |
|---|---|---|---|
| Adogen ® 448E-83HM[1] | 4.54 | 7.97 | 4.54 |
| Varisoft ® 445 Imidazoline[2] | 3.40 | 6.21 | 3.40 |
| Adogen ® 441[3] | 0.57 | 0.97 | 0.57 |
| Polydimethyl Siloxane (55%) | 0.32 | 0.61 | 0.32 |
| Silicone DC 1520 (20%) | 0.015 | 0.015 | 0.015 |
| Perfume (capsules) | 0.84(5) | 0.90(6) | 0.84(7) |
| Perfume (unencapsulated)[4] | — | 0.30 | 0.30 |
| Varonic ® T 220 D | 0.10 | 0.43 | 0.10 |
| Kathon ® | 0.034 | 0.034 | 0.034 |
| Tenox ® S-1 | — | 0.025 | — |
| Hydrochloric Acid (31.5%) | 0.62 | 1.25 | 0.62 |
| Calcium Chloride 25% Solution | 0.003 | 1.10 | 0.003 |
| Water | Balance | Balance | Balance |

[1] A mixture of ditallowalkyl dimethylammonium chloride and monotallowalkyl trimethylammonium chloride.
[2] Di long chain (tallow) alkyl imidazolinium softener.
[3] Monotallowalkyl trimethylammonium chloride.
[4] The unencapsulated perfume contains: 20% phenyl ethyl alcohol; 10% paramethoxy benzaldehyde; 30% hexyl cinnamic aldehyde; 20% 2,4-dinitro 3-methyl 6-tertiary butyl anisole; and 20% benzyl acetate.

The base product is made by a process that is similar to processes used for commercial products and the colorants which have been dissolved in water are simply added to the finished product with a mixer that provides high shear mixing. The microcapsules are evenly dispersed by moderate mixing action.

A sample (68 ml) of the fabric conditioner containing perfume microcapsules is added directly to the rinse cycle of a washing machine containing fabrics. After the rinse and spin cycles are complete the conditioned fabrics are dried in an electric tumble dryer for 50 minutes. The fabrics now contain higher levels of volatile perfume ingredients than fabrics treated with fabric conditioner containing the same perfume which is not encapsulated and this gives the fabrics greater freshness.

For example, use of Composition G will result in about 10 times more perfume on the fabrics after machine drying than would be present if the perfume were not encapsulated. Furthermore, odor grades by trained evaluators, using a scale from 1 to 10, will be about 1.5 grades higher. Similar, but lesser, benefits can also be obtained when the fabrics are dried on a clothes line.

What is claimed is:

1. Microcapsules containing a central hydrophobic liquid core having a diameter of greater than about 50 microns and less than about 350 microns, said core being surrounded by a wall having a thickness of from about 2 to about 50 microns at the thinnest point, said wall having from about 1% to about 25% by weight of the amount of said core of wall inclusion particles which have diameters of less than about 15 microns, and said inclusion particles have essentially the same composition as said central hydrophobic liquid core.

2. The microcapsules of claim 1 wherein said core has a diameter of from about 75 to about 300 microns and said wall has a thickness of from about 5 to about 25 microns at the thinnest point.

3. The microcapsules of claim 2 wherein said core has a diameter of from about 100 to about 250 microns.

4. The microcapsules of claim 2 wherein the diameters of said inclusion particles are no more than about 25% of the diameter of said core.

5. The microcapsules of claim 2 wherein the diameters of said inclusion particles are no more than about 15% of the diameter of said core.

6. The microcapsules of claim 2 wherein the diameters of said inclusion particles are no more than about 10% of the diameter of said core.

7. The microcapsules of claim 1 wherein the diameters of said inclusion particles are no more than about 25% of the diameter of said core.

8. The microcapsules of claim 1 wherein the diameters of said inclusion particles are no more than about 15% of the diameter of said core.

9. The microcapsules of claim 1 wherein the diameters of said inclusion particles are no more than about 10% of the diameter of said core.

10. The microcapsules of claim 1 wherein the total amount of said inclusion particles is from about 3% to about 20% by weight of the amount of said core.

11. The microcapsules of claim 1 wherein said wall is prepared by coacervation in the presence of both a population of large particles corresponding to said core and a population of small particles corresponding to said wall inclusion particles.

* * * * *